United States Patent [19]

Telfair et al.

[11] Patent Number: 5,782,822
[45] Date of Patent: Jul. 21, 1998

[54] METHOD AND APPARATUS FOR REMOVING CORNEAL TISSUE WITH INFRARED LASER RADIATION

[75] Inventors: William B. Telfair, San Jose, Calif.; Paul R. Yoder, Jr., Norwalk, Conn.; Hanna J. Hoffman, Palo Alto, Calif.

[73] Assignee: IR Vision, Inc., San Jose, Calif.

[21] Appl. No.: 549,385

[22] Filed: Oct. 27, 1995

[51] Int. Cl.$^6$ .................................................. A61N 5/02
[52] U.S. Cl. ...................... 606/5; 606/2; 606/3; 606/10; 606/14
[58] Field of Search .............................. 606/4, 5, 6, 10, 606/11, 12, 13, 14, 2, 3

[56] References Cited

U.S. PATENT DOCUMENTS

| | | |
|---|---|---|
| 4,169,663 | 10/1979 | Murr . |
| 4,461,294 | 7/1984 | Baron . |
| 4,665,913 | 5/1987 | L'Esperance . |
| 4,669,466 | 6/1987 | L'Esperance . |
| 4,720,189 | 1/1988 | Heynen et al. . |
| 4,732,148 | 3/1988 | L'Esperance . |
| 4,896,015 | 1/1990 | Taboada et al. . |
| 4,907,586 | 3/1990 | Bille et al. . |
| 4,911,711 | 3/1990 | Telfair et al. . |
| 4,968,130 | 11/1990 | Hideshima et al. . |
| 5,102,409 | 4/1992 | Balgorod . |
| 5,108,388 | 4/1992 | Trokel . |
| 5,349,590 | 9/1994 | Amirkhanian . |
| 5,350,374 | 9/1994 | Smith . |
| 5,360,424 | 11/1994 | Klopotek . |
| 5,474,548 | 12/1995 | Knopp et al. . |
| 5,520,679 | 5/1996 | Lin ........................................... 606/5 |

FOREIGN PATENT DOCUMENTS

| | | |
|---|---|---|
| 0 602 756 A1 | 6/1994 | European Pat. Off. . |
| 2 622 426 A | 10/1988 | France . |
| 35 40 763 A1 | 5/1987 | Germany . |
| 42 32 915 A1 | 4/1994 | Germany . |
| WO 93/14817 | 8/1993 | WIPO . |
| WO 94/18883 | 2/1994 | WIPO . |
| 95/27453 A | 10/1995 | WIPO . |

OTHER PUBLICATIONS

Seiler, Theo, et al., "The potential of an infrared hydrogen fluoride (HF) laser (3.0 um) for corneal surgery." Lasers in Ophthalmology, vol. 1, No. 1, pp. 49–60 (1986).

Stern, David, et al., "Infrared Laser Surgery of the Cornea Studies with a Raman–shifted Neodymium:YAG Laser at 2.80 and 2.93 um." Ophthamology, Oct. 1988, vol., 95, No. 10.

Dingus, R.S., et al., "Grüneisen–stress induced ablation of biological tissue." SPIE vol. 1427 Laser–Tissue Interaction II (1991).

European Patent Office, "European Search Report", 14 May 1997, pp. 1–2.

(List continued on next page.)

*Primary Examiner*—David M. Shay
*Assistant Examiner*—Sonya Harris-Ogugua
*Attorney, Agent, or Firm*—Cummings & Lockwood

[57] ABSTRACT

A surgical technique for removing corneal tissue with scanned infrared radiation is disclosed which utilizes short mid-infrared laser pulses to provide a tissue removal mechanism based on photospallation. Photospallation is a photomechanical ablation mechanism which results from the absorption of incident radiation by the corneal tissue. Since photospallation is a mechanical ablation process, very little heat is generated in the unablated adjacent tissue. The disclosed surgical system includes a scanning beam delivery system which allows uniform irradiation of the treatment region and utilizes low energy outputs to achieve controlled tissue removal. A real-time servo-controlled dynamic eye tracker, based on a multiple-detector arrangement, is also disclosed which senses the motion of the eye and provides signals that are proportional to the errors in the lateral alignment of the eye relative to the axis of the laser beam. Temporal and frequency discrimination are preferably utilized to distinguish the tracking illumination from the ambient illumination and the surgical laser beam.

26 Claims, 7 Drawing Sheets

OTHER PUBLICATIONS

European Patent Office, "Annex To The European Search Report", 14 May 1997, pp. 1–2.

Qiushi Ren, et al., Axicon: A New Laser Beam Delivery System for Corneal Surgery, IEEE Journal of Quantum Electronics, Dec., 1990, No. 12, New York, pp. 2305–2308.

Bende, T., Kriegerowski, M., and Seiler, T., "Photoablation in different ocular tissues performed with an erbium:YAG laser," Lasers in Ophthalmology, 2, 263–269 (1989).

Abel, T., Hirsch, J., and Harrington, J. A., "Hollow Glass Waveguides for Broadband Infrared Transmission," Optics Letters, 19, 1034–1036, (1994).

Jacques, S.L., "Laser–Tissue Interactions: Photochemical, Photothermal, and Photomechanical," Lasers in General Surgery, 72(3), 531–558 (1992).

Jean, B., M.D., Ph.D., Kriegerowski, M., M.D., Matallana, M., Bende, T., Ph.D., Correction of Myopia with Er:YAG Laser Fundamental Mode Photorefractive Keratectomy, Journal of Refractive Surgery, vol. 11 (1995).

Lian, J., Wang, K., Effects of Er:YAG laser of different pulse widths on rabbit corneas, SPIE, vol. 2393 160–166 (1995).

Lin, J.T., "Mini–Excimer Laser Corneal Reshaping Using A Scanning Device," SPIE Proceedings, vol. 2131, Medical Lasers & Systems III (1994).

Munnerlynn, C. R., Koons, S. J., and Marshall, J., "Photo-Refractive Keratectomy: a technique for laser refractive surgery," J. Cataract Refract. Surg., 14(1):46–52 (1988).

Pettit, G. H., Ediger, M. N., and Weiblinger, R. P., "Excimer laser ablation of the cornea," Optical Engineering, 34, 661–667 (1995).

Peyman, G. A., Badaro, R. M., and Khoobehi, B., "Corneal ablation in rabbits using an infrared (2.9um) erbium–YAG laser," Ophthalmology, 96, 1160–1170 (1989).

Ren, Q., Keates, R. H., Hill, R. A., and Berns, M. W., "Laser Refractive Surgery; a review and current status," Optical Engineering, 34, 642–660 (1995).

Ren, Q., Simon, G., Parel, J.M., "Ultraviolet Solid–state Laser (213nm) PhotoRefractive Keratectomy," Ophthalmology, 100, 12, 1828–1834 (1993).

Ren, Qiushi et al., "Mid–Infrared Laser Ablation of the Cornea: A Comparative Study," Lasers in Surgery and Medicine 12:274–281 (1992).

Seiler, T., and Wollensak, J., "Fundamental mode photoablation of the cornea for myopic correction," Lasers and Light in Ophthalmology, 5, 4, 199–203 (1993).

Walsh, J. T., Flotte, T. J., and Deutsch, T. F., "Er:YAG laser ablation of tissue: effect of pulse duration and tissue type on thermal damage," Lasers Surgical Medicine, 9, 314–326 (1989).

Wang, Kang–sun, Li, Qi, and Lan, Zhi–lin, "Comparison of Er:YAG and Excimer laser corneal ablation in rabbits," Lasers in Ophthalmology, 6, 69–75 (1994).

Webb, R.H., Penny, C.M., Thompson, K.P., "Measurment of Ocular Local Wavefront Distortion with a Spatially Resolved Refractometer," Applied Optics, 31, 19, 3678–3686, (1992).

Product brochure, Orbscan, "A Pan Corneal Slit Topography & Pachymetry System," Orbtek, Salt Lake City, UT 84115 (undated).

Product brochure, Visx Twenty/Twenty Excimer Laser System, "Reshaping Vision," Alcon International, Alcon Laboratories, Inc. Fort Worth, TX 76134 (1992).

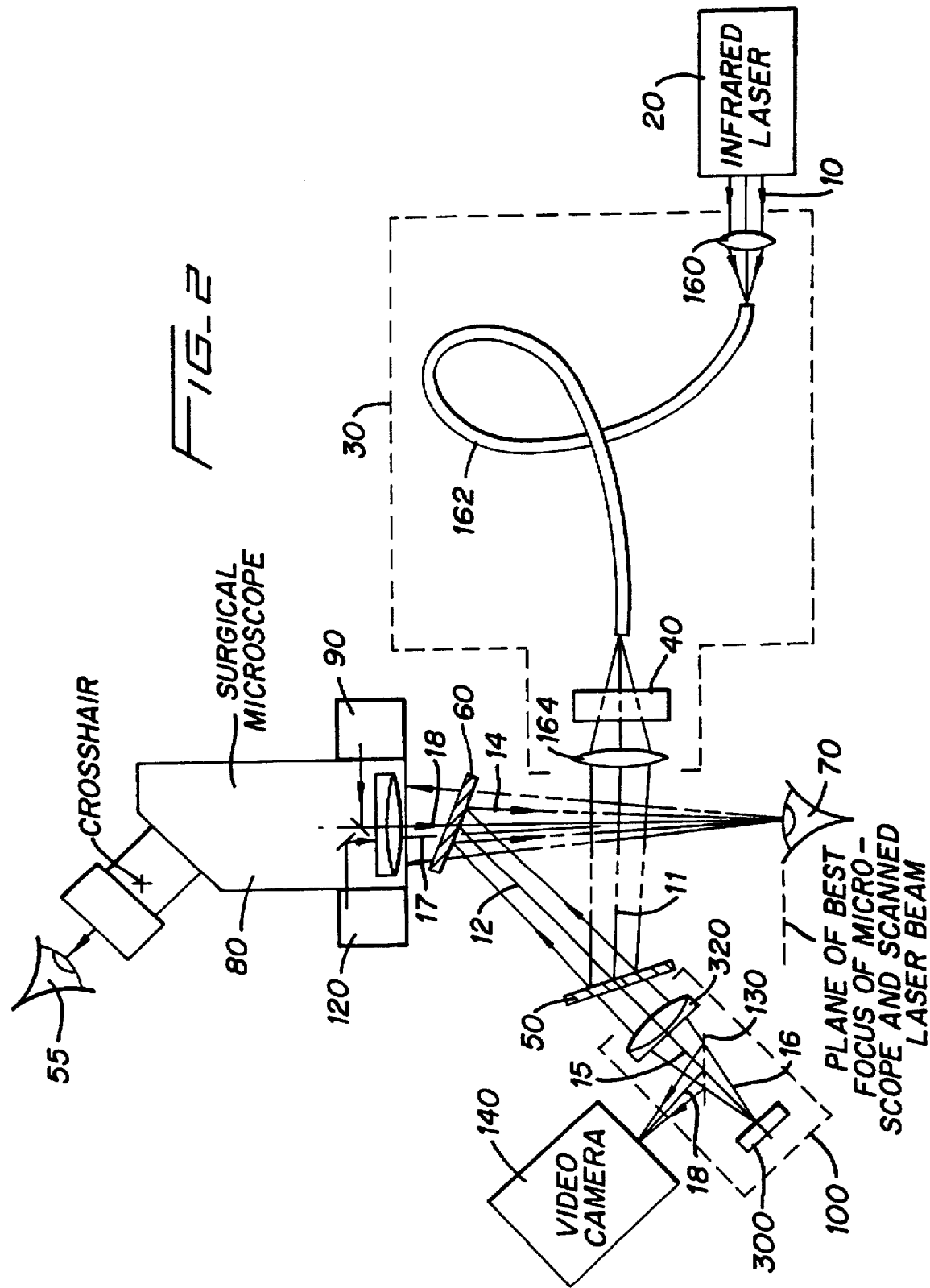

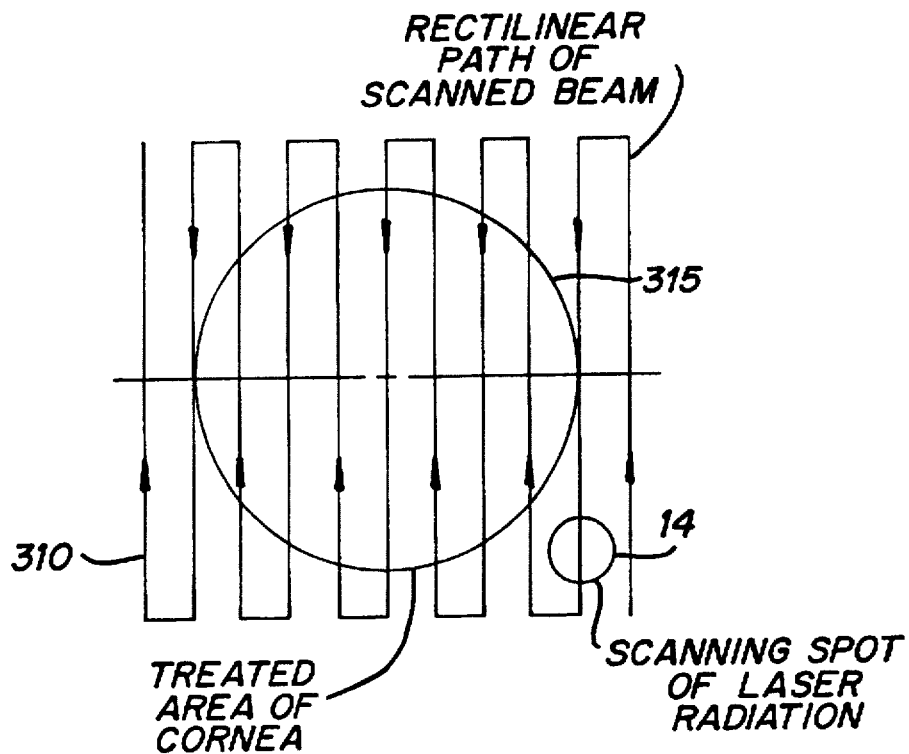
FIG_3A
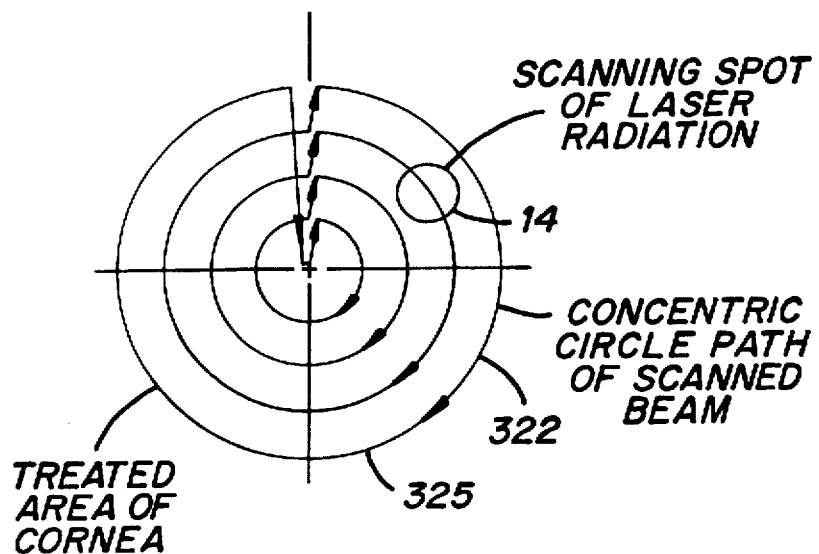
FIG_3B

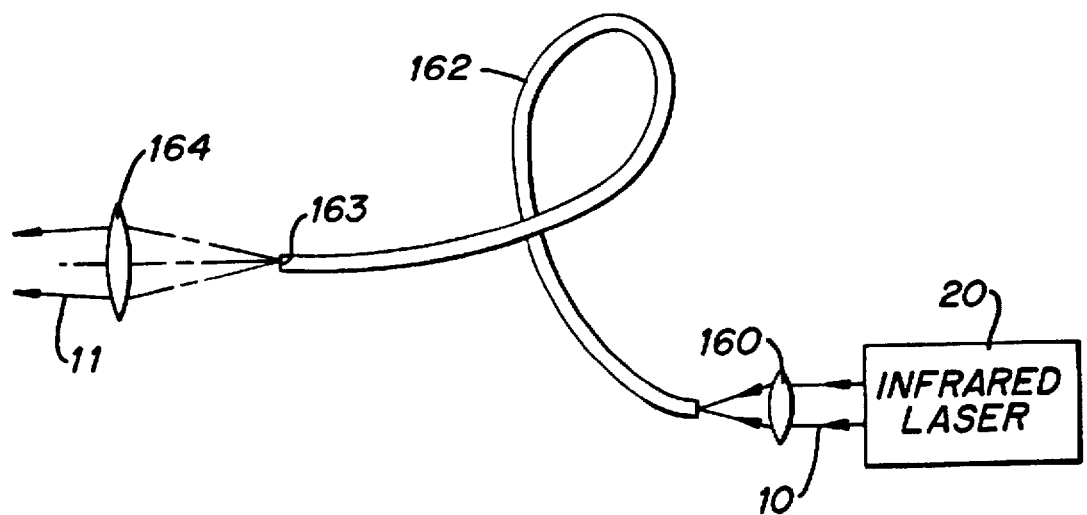
FIG_5A
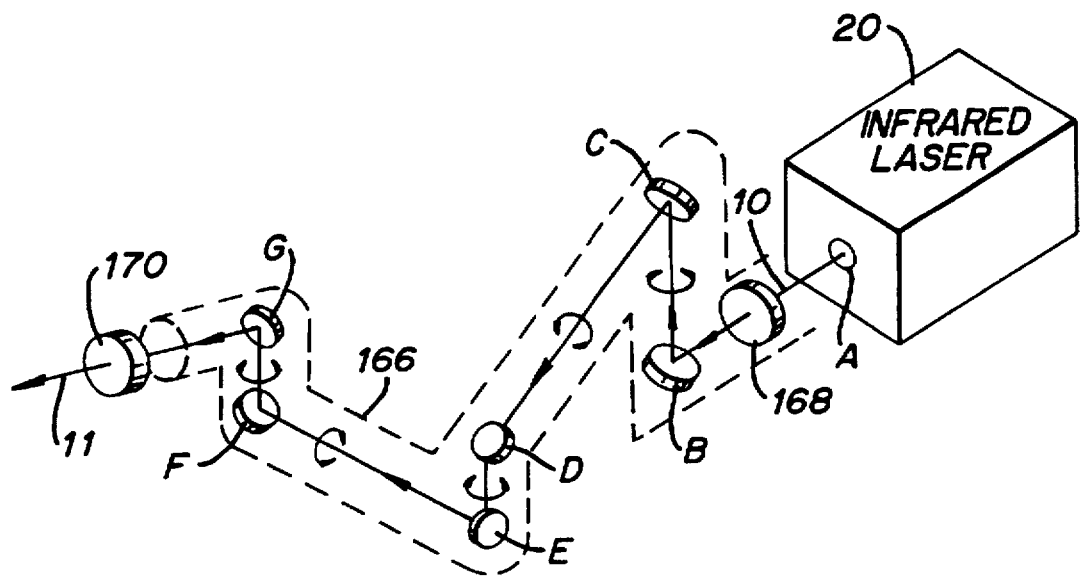
FIG_5B

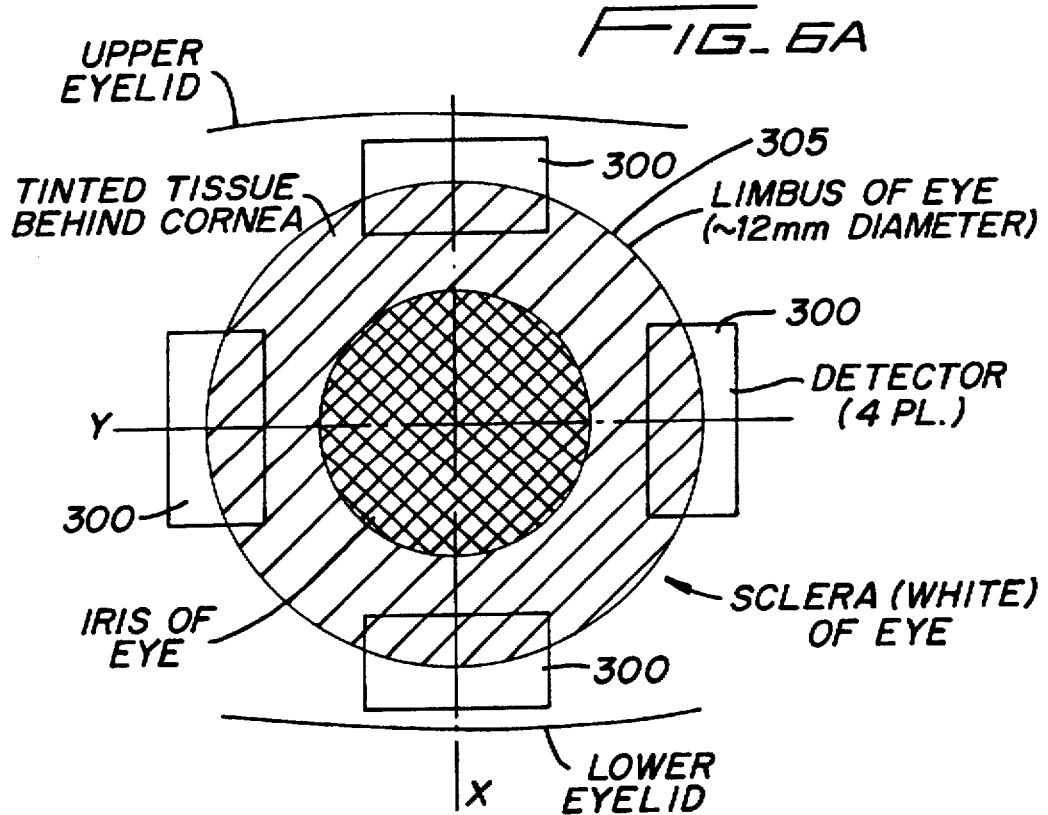
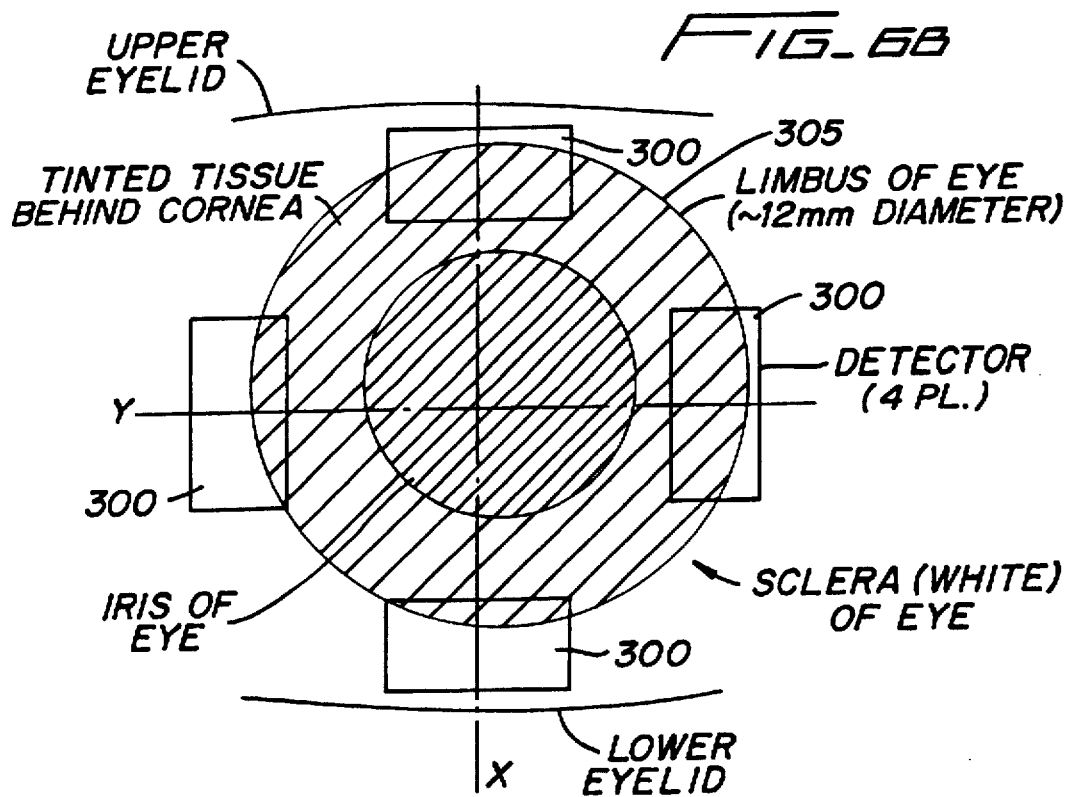

METHOD AND APPARATUS FOR REMOVING CORNEAL TISSUE WITH INFRARED LASER RADIATION

FIELD OF THE INVENTION

The present invention relates to laser surgical techniques for modifying the corneal surface of the eye, and more particularly, to laser surgical techniques, collectively known as photorefractive keratectomy or PRK, which direct reshaping of the cornea by means of selective volumetric removal of corneal tissue.

BACKGROUND OF THE INVENTION

In recent years, numerous corneal sculpting techniques and related apparatus have been disclosed for correcting visual deficiencies such as near-sightedness, far-sightedness, and astigmatism. In addition, corneal sculpting techniques have also been utilized for therapeutic interventions in a number of pathologic conditions involving the cornea. For example, U.S. Pat. Nos. 4,665,913, 4,732,148, and 4,669,466 to L'Esperance, and U.S. Pat. No. 5,108,388 to Trokel, describe methods for achieving optical correction through reshaping of the anterior corneal surface. In addition, a number of prototype instruments for affecting refractive surgery have recently become commercially available, such as the Model 2020 from Visx of Santa Clara, Calif. and the Model Exci-Med 200 from Summit of Watertown, Mass.

These commercial devices, as well as most corneal sculpting methods and devices which have been disclosed and manufactured to date, utilize ultraviolet (UV) radiation with a wavelength which is preferably less than 200 nanometers. For example, many of these devices utilize an Argon Fluoride excimer laser operating at 193 nm. Generally, radiation at such short ultraviolet wavelengths is characterized by high photon energy, namely, greater than 6 eV, which, upon impact with tissue, causes molecular decomposition, i.e., the direct breaking of intramolecular bonds. The photochemical nature of this mechanism has the advantage of producing minimal collateral thermal damage in cells adjacent to the surgical site, since the broken molecules generally leave behind only small volatile fragments which evaporate without heating the underlying substrate. Furthermore, the depth of decomposition for each laser pulse is typically very small, i.e., less than 1 micron, thus achieving accurate tissue removal with minimal risk of damage to the underlying structures from UV radiation.

In view of this small depth of penetration, coupled with the need to remove sufficient depth of tissue while minimizing the overall time for the surgical procedure, the majority of corneal sculpting techniques utilizing the excimer laser employ "wide area ablation". Generally, wide area ablation utilizes a laser beam with a relatively large spot size to successively remove thin layers of corneal tissue. The spot size is generally of a size sufficient to cover the entire optical zone of the cornea, namely, a region of 5 to 7 millimeters in diameter. Consequently, to assure required flux densities on the cornea, relatively high energy output UV lasers are typically required. It has been found that to assure a flux density of at least 150 mJ/cm$^2$, for a reasonable ablation rate of at least 0.2 microns/pulse, a 200 mJ UV laser is required. Such lasers, however, tend to be prohibitively large and expensive systems.

Furthermore, efficacious wide area ablation requires that the projected beam be spatially homogenous and uniform to achieve the desired smooth corneal profiles. Accordingly, additional beam shaping devices, such as rotating prisms, mirrors, or spatial integrators, must be employed within the excimer beam delivery systems. For a more detailed discussion of beam shaping and delivery systems, see, for example, U.S. Pat. No. 4,911,711 to Telfair, incorporated by reference herein. Of course, such a multiplicity of optical elements contributes to overall transmission loss, while adding substantial optical complexity, cost, and maintenance requirements to the system.

Alternative techniques based on utilization of a scanning UV laser beam have been proposed to achieve controlled and localized ablation of selected corneal regions of the cornea. In the scanning approach, a relatively small laser spot is scanned rapidly across the cornea in a predefined pattern and accumulatively shapes the surface into the desired geometry. For a more detailed discussion of laser scanning techniques employing excimer lasers, see U.S. Pat. No. 4,665,913 to L'Esperance or Lin, J. T., "Mini-Excimer Laser Corneal Reshaping Using a Scanning Device," SPIE Proceedings, Vol. 2131, Medical Lasers & Systems III (1994). A scanning approach may offer a number of advantages, including lower power and energy requirements, added flexibility for refractive corrections and smooth ablation profiles, without the need for spatially uniform output beam profiles. For example, a laser scanning technique allows a tapered optical treatment zone to be achieved, which may have advantages for the correction of high myopia, for performing therapeutic tissue removal and for treating areas up to 9 millimeters in diameter which may be required for the correction of hyperopia.

While laser surgical techniques based on the excimer laser have proved beneficial for many applications, such techniques suffer from a number of limitations, which, if overcome, could significantly advance the utility of optical laser surgery. For example, techniques based on excimer lasers utilize toxic gases as the laser medium, suffer from persistent reliability problems, require lossy optics in the delivery systems, and suffer from the possibility that the UV radiation is potentially mutagenic through secondary fluorescence, which may cause undesirable long term side effects to the unexposed tissues of the eye.

Accordingly, alternatives to the excimer laser have been suggested in recent years which involve frequency-shifted radiation from a solid state laser. Current limitations of nonlinear elements used as frequency-shifting devices, however, place a lower limit of approximately 205 nm on the available wavelengths of such lasers, which may be too close to the mutagenic range, which exhibits a peak at 250 nm. In addition, multiply-shifted laser devices also face certain difficulties in providing the requisite energy outputs and are fairly complex and cumbersome, leading again to potential laser reliability problems, as well as added cost and maintenance.

More recently, a more attractive alternative has been suggested by T. Seiler and J. Wollensak, "Fundamental Mode Photoablation of the Cornea for Myopic Correction", *Lasers and Light in Ophthalmology*, 5, 4, 199–203 (1993), involving mid-infrared wavelengths and, in particular, radiation around 3 microns corresponding to the absorption peak of water, the main constituent of the cornea. One solid state laser in particular, the Erbium:YAG laser (Er:YAG), emits radiation at a wavelength of 2.94 microns, corresponding to an absorption coefficient of over 13000 cm$^{-1}$ in water. This high absorption results in a small region of impact with potentially less than two micron penetration depths.

Contrary to the photoablation mechanism associated with the excimer laser, i.e., photochemical decomposition, which is due to energy absorption in molecular bonds, ablation with the Er:YAG laser is attributed to photovaporization, or photothermal evaporation, of water molecules. This thermal heat induces a phase change, and thus a sudden expansion of the tissue material, thereby ablating the corneal surface tissue.

In addition, erbium lasers are more attractive for clinical applications than excimer lasers, since they are compact, efficient and can deliver higher beam quality radiation, which allows for less lossy beam delivery systems and superior optical coupling properties. Further, the photovaporization process is inherently more efficient than photodecomposition, allowing for removal of up to 3 microns of tissue at a time and thereby resulting in a faster surgical operation. Mid-infrared radiation is also compatible with fiber delivery, a potentially attractive method of decoupling the source laser from the delivery system which makes it more suitable for the operating room. Finally, radiation from an Er:YAG laser is not mutagenic, relieving the potential for deleterious long-term side effects.

The Er:YAG laser-based corneal sculpting system described by Seiler and Wollensak is based on wide area ablation. This system aims to exploit the gaussian beam profile of the laser beam to achieve a refractive correction with each pulse, using a minimal number of pulses. An alternative system which also relies on wide area ablation is described in PCT Application No. 93/14817 to Cozean et al., which relies on a sculpting filter to control the intensity of the radiation delivered to the cornea and hence the amount of tissue removal.

While providing a number of advances over prior techniques, the Er:YAG laser techniques described by Seiler and Wollensak and Cozean et al. both suffer from a number of potential drawbacks, common to wide area ablation techniques, including the need for a smooth and uniform beam profile, a large pulse energy, and/or a complex filter control system. These systems assumed that the ablation process is a linear process, i.e., that a portion of the beam with a larger energy density will remove a larger depth of tissue. This has been shown, however, to be an incorrect assumption for the excimer ablation process, and may also be an incorrect assumption for the Er:YAG ablation process.

In addition to the limitations previously discussed, all such prior techniques for delivering and controlling a mid-infrared laser beam are subject to one shortcoming in particular, namely, the potential for thermal damage to unablated regions of the eye, due to excessive energy density required by these systems and the large shock waves generated by the high energy pulses required to ablate wide areas. In addition, due to the need for high pulse energy and high beam quality, such prior systems typically exhibit optical configurations that are generally not conducive to ease of manufacturing and are difficult to maintain and service.

As is apparent from the above discussion, a need exists for an improved method and apparatus for surgically treating corneal tissue based on the controlled removal of tissue. A further need exists for an improved method and apparatus for reducing myopic, hyperopic and/or astigmatic conditions of the eye using a low cost solid state laser. Yet another need exists for a method and computer-controlled apparatus for scanning mid-infrared laser radiation across the outer surface of the eye and the underlying Bowman's layer and stroma for the purpose of reducing refractive errors of the eye and for the purpose of treating tissue at or near the surface of the cornea. A further need exists for a method and apparatus for surgically treating corneal tissue, having an improved eye tracking mechanism.

SUMMARY OF THE INVENTION

Generally, according to aspects of the invention, a surgical method and apparatus for removing corneal tissue with mid-infrared radiation are provided. The surgical method and apparatus utilize short laser pulses scanned over a region of the cornea to yield a tissue removal mechanism based on photospallation. Photospallation is a photomechanical ablation mechanism which results from the absorption of incident radiation by the corneal tissue. When the corneal tissue absorbs the infrared radiation, a bipolar oscillating shock wave is created, which alternately compresses and stretches the corneal tissue. Tissue fragments are torn apart and ejected by the shock wave during the stretching phase.

In accordance with one feature of the present invention, the laser delivery system includes a laser source, such as a Q-switched Er:YAG laser, which emits pulsed radiation in the mid-infrared spectral region with an energy density capable of causing ablation of corneal tissue. In a preferred embodiment, the laser emits radiation of approximately 3 microns, corresponding to the maximal absorption coefficient of water, the main constituent of corneal tissue. The laser source preferably emits radiation at discrete pulses of less than 50 nanoseconds at a repetition rate of approximately 5 to 100 Hertz. The short laser pulses reduce the undesirable thermal damage of surrounding tissue to insignificant levels. The energy in each pulse is preferably on the order of 5 to 30 mJ.

The laser beam is preferably scanned over a specific central region of the surface of the cornea in a predefined pattern by a scanning beam delivery system so as to selectively remove tissue at various points within the scanned region and thereby reshape the corneal tissue in a predictable and controlled fashion. The scanning beam delivery system preferably consists of a controllable tilt mirror assembly to direct and aim the beam over the surface of the cornea. A variety of predefined scan patterns may be utilized to achieve controlled photospallation of the cornea, including the epithelium, Bowman's layer, and the stroma in accordance with the desired changes in the shape of the cornea.

In accordance with a further aspect of the present invention, the laser spot size and spacing associated with a given scan pattern may be varied prior to each procedure according to certain nomograms correlating the required degree of pulse overlap with the depth of ablation, consistent with maximizing the speed of the operation and the requisite smoothness of the ablated corneal surface. A given scan pattern preferably uniformly irradiates a treatment region with minimal discernible lines of overexposed or underexposed tissue lying between scans. One or more discontinuous scan patterns may be utilized to distribute the pulse over the entire treatment region in each time interval, thereby distributing residual heat over the entire region and minimizing temperature rise in any localized area.

Further, in accordance with a preferred embodiment of the invention, an eye tracking system is further provided in conjunction with the scanning beam delivery system, to compensate for eye motion during the surgical procedure. The eye tracking system senses the motion of the eye and provides signals that are proportional to the errors in lateral alignment of the eye relative to the axis of the laser beam. Lateral motion of the eye is detected by illuminating the eye with tracking illumination and forming an image of a significant feature of the eye, such as the limbus, on an array of detectors. According to a feature of the present invention, the array of detectors includes at least four detectors centered vertically and horizontally around the center of the detector array.

In operation, when the significant feature of the eye is centered with respect to the axis of the laser beam, the image of the significant feature will be centered on the detector array. A null signal is generated by the detector array which serves to maintain the axis of the laser beam in its current position. When the eye is not centered with respect to the axis of the laser beam, however, the image formed on the detector array will also not be centered. The detector array will generate an error signal which causes the laser beam to be deflected to ensure that it is properly applied to the corneal tissue.

The tracking illumination is preferably chosen in the near infrared range so that it may be discriminated from ambient illumination and the laser beam. In addition, the tracking illumination is preferably modulated at a predefined temporal frequency to further discriminate the tracking illumination from the ambient illumination and the laser beam. Red or near infrared filters may be positioned in front of the detectors in the array to further enhance the contrast of the significant feature of the eye to be detected, such as the limbus.

According to further features of the invention, a corneal topography device may be included in the surgical apparatus for evaluating the shape of the corneal tissue to assist in pre-op or post-operative measurements. Alternatively, a spatially resolved refractometer may be included for evaluating the refraction of the corneal tissue. In various embodiments of the invention, the above-described alignment methods may be utilized to incorporate active feedback control from the topographic or refraction mapping instrument so as to provide further control over the course of the surgical procedure.

A more complete understanding of the present invention, as well as further features and advantages of the invention, will be obtained by reference to the detailed description and drawings.

BRIEF DESCRIPTION OF THE DRAWINGS

FIG. 2 is an expanded schematic diagram of the optical components of FIG. 1;

FIGS. 3(a) and 3(b) illustrate scanning patterns for the laser beam passing over the cornea;

FIGS. 5(a) and 5(b) illustrate mechanisms for transferring the laser beam from the laser system to the surgical apparatus;

FIGS. 6(a) and 6(b) illustrate images of the eye in an aligned and unaligned position, respectively, with respect to the detector array of an integral eye tracker.

DETAILED DESCRIPTION

Figure 1:
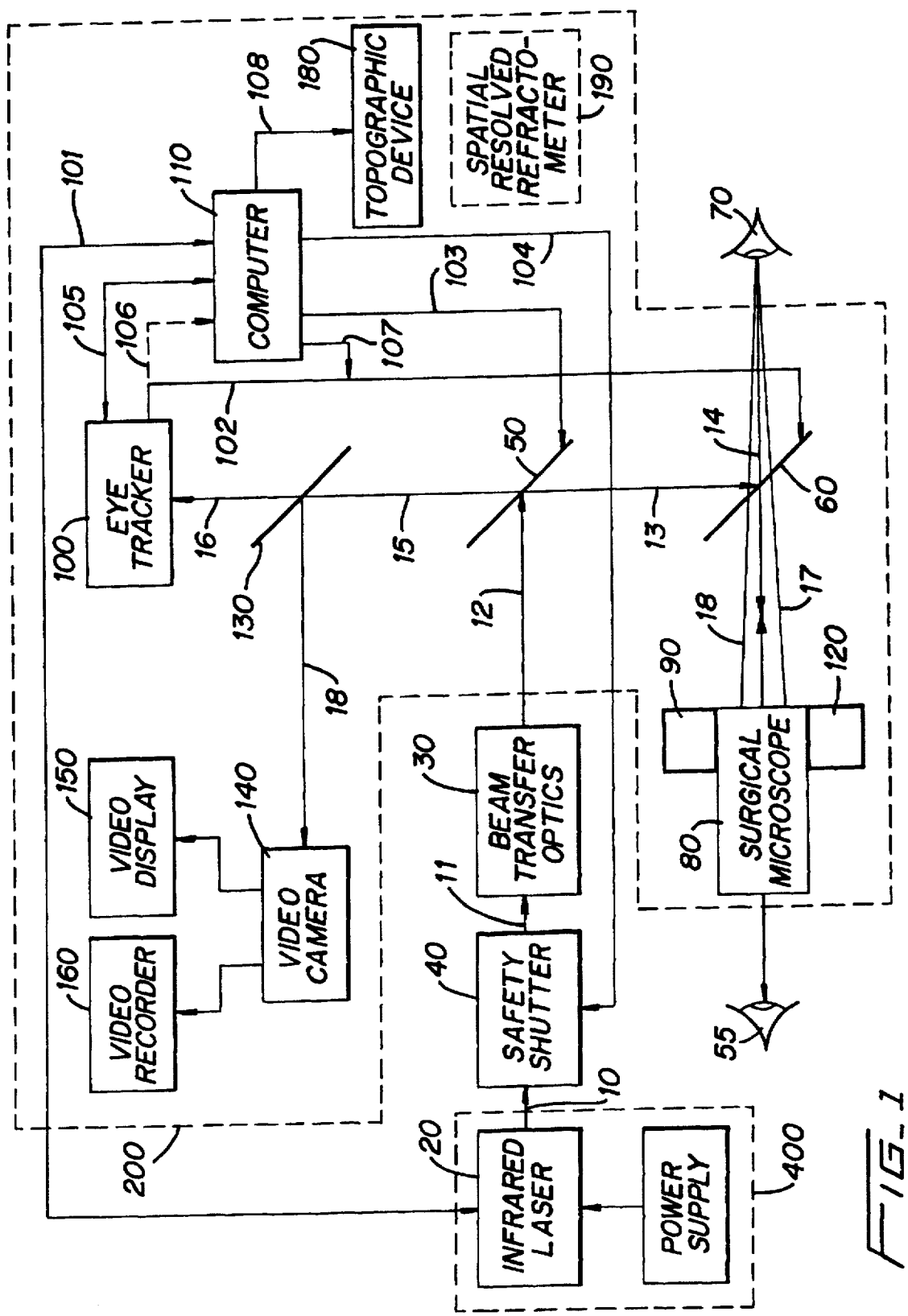
FIG. 1 is a block diagram illustrating the functional relationship of optical, mechanical, and electrical components of apparatus incorporating features of the present invention.

As shown in FIGS. 1 and 2, a surgical apparatus 200 includes an infrared laser source 20 and an optical assembly, including, in sequence, beam transfer optics 30, discussed below in conjunction with FIG. 5, a safety shutter 40, and partially-transmitting mirrors 50 and 60, which cooperate to focus an output beam 10 upon the cornea of a patient's eye 70, for correcting curvature of the cornea or for affecting therapeutic interventions. The laser source 20 is preferably a mid-infrared laser generating short laser pulses, to yield a tissue removal mechanism based on photospallation, discussed below. The laser beam 10 is preferably scanned over a specific central region of the surface of the cornea in a predefined manner, as discussed below in conjunction with FIGS. 3(a) and 3(b), so as to selectively remove tissue at various points within the cornea and thereby cause the curvature of the cornea to change in a predictable and controlled fashion.

According to one feature of the invention, the laser source 20 is preferably a solid state laser, which emits pulsed radiation in the mid-infrared spectral region with an energy density capable of causing ablative decomposition of corneal tissue. As used herein, the term "solid state laser" includes a diode laser. Preferably, the laser emits radiation at a corneal absorption peak, i.e., at a wavelength of approximately 3 microns, such as 2.7 to 3.1 microns, corresponding to the maximal absorption coefficient of water, the main constituent of the corneal tissue. It has been found that absorption of laser energy by the corneal tissue of the eye 70 at such a wavelength results in complete absorption within 1 to 2 microns of tissue depth. As discussed further below, it has been found that the combination of shallow absorption depths and short radiation pulses reduces the undesirable thermal damage of surrounding tissue to insignificant levels.

PHOTOSPALLATION

As previously indicated, according to a feature of the present invention, the surgical technique disclosed herein, whereby corneal tissue is irradiated with short pulses of a scanned mid-infrared laser beam, is based on a concept referred to as photospallation. Generally, photospallation is a photomechanical ablation mechanism which results from the absorption of incident radiation by the corneal tissue. When the corneal tissue absorbs the infrared radiation, a bipolar oscillating shock wave is created, which alternately compresses and stretches the corneal tissue, ejecting the tissue fragments torn apart during the stretching phase. For a more detailed discussion of photospallation, see Jacques, S. L., "Laser-Tissue Interactions: Photochemical, Photothermal, and Photomechanical," *Lasers in General Surgery*, 72(3), 531–558 (1992), incorporated by reference herein. Since photospallation is a mechanical ablation process, there is very little heat generated in the adjacent tissue left behind after the ablation.

The laser source 20 may be embodied as a Q-switched Er:YAG laser, which delivers a beam of mid-infrared radiation at or near a wavelength of 2.94 microns. Alternatively, the laser source 20 may be embodied as a Neodemium or Holmium doped laser which is frequency shifted by an optical parametric oscillator (OPO) to emit radiation of approximately 3 microns. Of course, substitution of other alternative laser sources with similar emission characteristics to that of the Er:YAG laser, as they become available, are included within the scope of this invention.

The laser source 20 preferably emits radiation at discrete pulses of less than 50 nanoseconds in duration at a repetition rate of 5 to 100 hertz. The laser pulses should be short enough such that lateral thermal damage of tissue adjacent to the irradiated region is limited to a region smaller than 2 microns wide, consistent with a photospallation process. In addition, the energy in each pulse of the laser 20 is preferably on the order of 5 to 30 mJ. Thus, the incident laser beam 14 will ablate tissue locally and thereby remove microscopic portions of the cornea.

LINE-OF-SIGHT

To correlate the eye's reference frame to that of the surgical instrument 200, as shown in FIGS. 1 and 2, it is necessary that the line-of-sight of eye 70 be substantially coincident with the propagation axis of the incident laser beam 14. As used herein, in accordance with customary definition, the term "line-of-sight" or "principal line of vision" refers to the chief ray of the bundle of rays passing through the pupil and reaching the fovea, thus connecting the fovea with the fixation point through the center of the entrance pupil. It will therefore be appreciated that the line-of-sight constitutes an eye metric defined directly by the patient, rather than through some external measurement of the eye and further, that the line-of-sight can be defined without ambiguity for a given eye and is the only axis amenable to objective measurement using cooperative patient fixation.

Since critical vision is by definition centered on the line-of-sight of the eye, irrespective of the direction in which the mechanical axis of symmetry of the eye is pointed, it is generally acknowledged that for best optical performance, the point marking the intersection of the line-of-sight with the cornea establishes the desired center for the optical zone of refractive procedures seeking to restore visual acuity. It is noted that the orientation of the line-of-sight of the eye 70, as shown in FIGS. 1 and 2, may be vertical, horizontal, or intermediate to those extremes as befitting comfortable positioning of the patient for surgery without affecting the validity of the invention.

During preparation for laser surgery on the cornea, the line-of-sight of the eye 70 must be aligned to coincide with the laser beam axis by two-axis lateral-translational adjustments, in a known manner, as directed by the surgeon 55. The surgeon 55 observes the eye 70 through a surgical microscope 80 and judges the degree of centration of the frontal image of the eye 70 with respect to a crosshair or other fixed reference mark indicating, as a result of prior calibration, the location of the axis of beam 14, in a known manner. The axial location of the eye 70 is also judged by the surgeon 55 by virtue of the observed degree of focus of the image of the eye 70 relative to the previously calibrated and fixed object plane of best focus for microscope 80. Directions from the surgeon 55 allow adjustment of the axial position of the cornea of eye 70 to coincide with the plane of best focus.

The required angular orientation of the line-of-sight of eye 70 is preferably established by directing the patient to observe and focus attention, i.e., fixate, on two coaxial illuminated targets (not shown) projected into the eye 70 by a fixation target device 90, which is preferably integrated into the microscope 80. The two targets appear to be located at different axial distances from the eye 70 of the patient and will have been previously calibrated in a known manner. For a description of a suitable calibration technique, see PCT application No. WO 94/07908 to Knopp and Yoder. In this manner, when the two targets (not shown) appear superimposed, the axis of the observing eye 70 will be substantially coincident angularly with the axis of the microscope 80 and also with the axis of laser beam 14.

In a preferred embodiment, small lateral motions of the patient's eye 70, i.e., less than 5 mm in either direction, that occur after the initial alignment performed in the manner described above, and throughout surgical treatment, are rendered inconsequential by virtue of the function of a two-dimensional eye tracker 100, discussed further below in conjunction with FIGS. 6 and 7. The eye tracker 100 senses the motion of the eye 70 and provides signals that are proportional to the errors in lateral alignment of the eye 70 relative to the axis of the laser beam 14. The signals generated by eye tracker 100 are converted into commands for small angular tilts of partially-reflecting mirror 60 that compensate for errors in the location of the eye 70. The small angular tilts serve to redirect beam 14 so as to make it coincide with the instantaneous position of the eye 70. The compensation commands are sent from electronics, discussed below in conjunction with FIG. 7, within the eye tracker 100 to mirror 60 by means of one or more data connections, collectively designated 102.

Illumination of the eye 70 to facilitate tracking by the eye tracker 100 is preferably accomplished by means of a coaxial illuminator 120, preferably integrated with the microscope 80, that projects a beam of light 17 at a small angle, on the order of 8°, with respect to the line-of-sight of the microscope 80. According to a feature of the invention, the nature, i.e., the wavelength and temporal modulation frequency, of the tracking beam 17 generated by illuminator 120 is preferably selected to maximize discrimination by the detectors and related electronic circuitry within eye tracker 100 of the tracking beam 17, from ambient room illumination and radiation from laser 20. In this manner, the ambient illumination and laser beam 14 will not possess the same temporal modulation nor spectral characteristics as the tracking beam 17, and will thus be virtually invisible to the tracking detectors.

In addition, as shown in FIG. 1, the surgical system 200 preferably includes a safety shutter 40 which closes automatically if the laser beam 14 fails to follow a prescribed path, if pulse energy-monitoring means provided within laser 20 indicates a malfunction of said laser or if the eye tracker 100 cannot follow the eye motion.

As shown in FIG. 1 and discussed further below, the surgical apparatus 200 preferably includes a video camera 140 that displays a real-time image of the patient's eye on a monitor 150 during pre-operation alignment and during surgical treatment and records the video image on a video recorder 160 for postoperative examination and documentation of the surgical procedure.

As shown in FIG. 1, the computer 110 includes multiple storage and control capabilities. Specifically, the computer 110 communicates and thereby controls the laser source 20 by means of a connection 101. In addition, the computer 110 drives the scanning mirror 50 by means of a connection 103, in accordance with stored scanning patterns and commands input to the computer 110 by the surgeon 55 or an assistant. A connection 104 between the computer 110 and the safety shutter 40 affects maximum safety of the patient, the surgeon, and attending personnel. The computer 110 monitors the operation and status of the eye tracker system 100 by means of a connection 105. Alternately, as shown in FIG. 1, computer 110 can be connected to the eye tracker 100 by means of connection 106 and a separate connection 107 can be provided from computer 110 to mirror 60 so that the computer 110 could directly control the position of the mirror 60. A further alternate configuration would allow the computer 110 to combine the scanning and eye tracking functions together onto a single mirror, such as the mirror 60, thereby removing the need for connection 103.

As discussed further below, the surgical apparatus 200 preferably includes a corneal topography device 180 or a spatially resolved refractometer 190, as shown in FIG. 1. A corneal topography device 180 may be used for evaluating the shape of the corneal tissue to assist in pre-op and post-op measurements of the eyes' shape or curvature. An alternate embodiment would include a spatially resolved refractometer (SRR) 190 to evaluate the refraction of the corneal tissue.

OPTICAL MIRRORS

It may be noted from examination of FIGS. 1 and 2 that the partially-reflecting natures of mirrors 50 and 60 play important roles in the proper function of the invention. In the case of mirror 50, laser radiation in beam 12 is reflected while radiation from eye tracker 100 is transmitted. This can be accomplished, for example, through use of what is commonly called a "hot mirror" coating on the surface of mirror 50. This coating is dichroic, in other words, the coating has different reflection and transmission characteristics for light of differing wavelengths. The radiation from laser 20 has a wavelength of approximately 2.9 microns and the mirror 50 should have a high reflectance at that wavelength. The radiation to eye tracker 100 preferably has a wavelength between 0.8 and 1.0 microns for which the coating of mirror 50 should have a high transmittance.

Similarly, the dichroic coating on mirror 60 is preferably selected to have high reflectance at the wavelength of laser 20 and approximately equal transmittance and reflectance at the visible wavelengths used by the surgeon's eye in observing the alignment of the eye with respect to the surgical apparatus and progress of the surgery, at the wavelength of the fixation target 90, and at the wavelength of the coaxial illuminator 120. This is possible since the visible range, the fixation target 90, and the illuminator 120 are adjacent in wavelength and far from the wavelength of laser 20. At both mirrors 50 and 60 the transmitted beams suffer small lateral displacements due to oblique incidence and the finite thickness of the mirror substrates, but these fixed displacements are easily compensated for in the design of the apparatus, as would be apparent to a person of ordinary skill in the art.

In addition, mirror 130, shown between beams 15 and 16 of FIGS. 1 and 2, is also preferably partially transmitting, although not dichroic. The coating on mirror 130 nominally has approximately equal reflectance and transmission characteristics at the wavelengths of the eye tracker light source 120 and throughout a significant portion of the visible spectral region. In this manner, a portion of the energy of beam 15 can be redirected as beam 18 into video camera 140, discussed above. It is understood that a beamsplitting prism, typically in the form of a cemented two-element cube with a partially-reflecting coating on an internal surface can be employed to provide the function of mirror 130.

SCANNING PATTERNS

As previously indicated, the surgical apparatus 200 of FIGS. 1 and 2 preferably provides a computer-controlled scanning motion of the focused laser beam 14 for sequentially irradiating contiguous small areas of the central portion of the cornea of eye 70 with pulses of mid-infrared laser radiation in predefined patterns, such as those illustrated in FIGS. 3(a) and 3(b). In each case, the region to be treated has a diameter of up to 9 mm. The size of the focused spot of laser radiation is preferably on the order of a 0.5 to 2.0 mm circumscribed diameter.

As shown in FIG. 3(a), a rectilinear or raster-scan 310 of the scanning spot of laser beam 14 covers a square area centered on the desired treatment region 315. The laser beam 14 is modulated "off" when the computer 110 predicts that the energy would impinge upon corneal tissue outside the desired treatment region 315. As shown in FIG. 3(b), the laser beam 14 scans in a concentric-circle pattern 322 that is centered on the desired treatment region 325. While the path of the laser beam 14 may be continuous from start to finish, as indicated in the illustrative modes of FIGS. 3(a) and 3(b), an alternative operational mode divides the pattern a list of location coordinates and covers the entire area in a discontinuous fashion in order to minimize residual thermal effects of the area adjacent to the scan path by cumulative irradiation in rapidly sequenced locations of the beam. In this embodiment, the scanner would have random access capability to each location.

In the illustrative modes shown in FIGS. 3(a) and 3(b), or in other continuous or discontinuous scan patterns which would be apparent to persons of ordinary skill in the art, based on the disclosure herein, adjacent scan paths nominally overlap in a controlled manner. In this manner, the entire treatment region 315, 325 is uniformly irradiated with minimal discernible lines of overexposed or underexposed tissue lying between the scans. It is noted that the discontinuous property of the sequence distributes the pulses over the entire area in each time interval which is short compared to the entire sequence, thereby better distributing any residual heat to the entire surface and minimizing the buildup of heat and any temperature rise in any localized area. Once the pattern is defined by the computer 110, the implementation of the delivery can be discontinuously distributed across the corneal surface for maximum surface smoothness and minimum thermal effect.

Scanning of the laser beam over the cornea surface is accomplished by a controlled tilting of the partially-reflecting mirror 50 about two axes so the reflected beam is deviated in an appropriate manner. This scanning motion is imparted to electrically-driven tilting mechanisms attached to mirror 50 under control of computer 110 upon initiation of the surgical treatment.

The velocity of the scan motion is varied at different points within the treatment area 315, 325 in accordance with an algorithm prescribed by the surgeon 55 to cause more or less ablation to take place locally, thereby causing the desired changes in refractive power of the cornea's anterior surface to correct the patient's vision defects. Correction of astigmatic, or cylindrical, errors can be accomplished by driving the scan mirror at different speeds as a function of rotational location about the propagation axis in the pattern. This allows the laser beam 14 to selectively ablate more tissue near one meridian of the corneal surface than near the orthogonal meridian. The nonsymmetric scan motion can be superimposed upon the normal symmetric pattern to simultaneously correct spherical and cylindrical refractive errors.

Figure 4A:
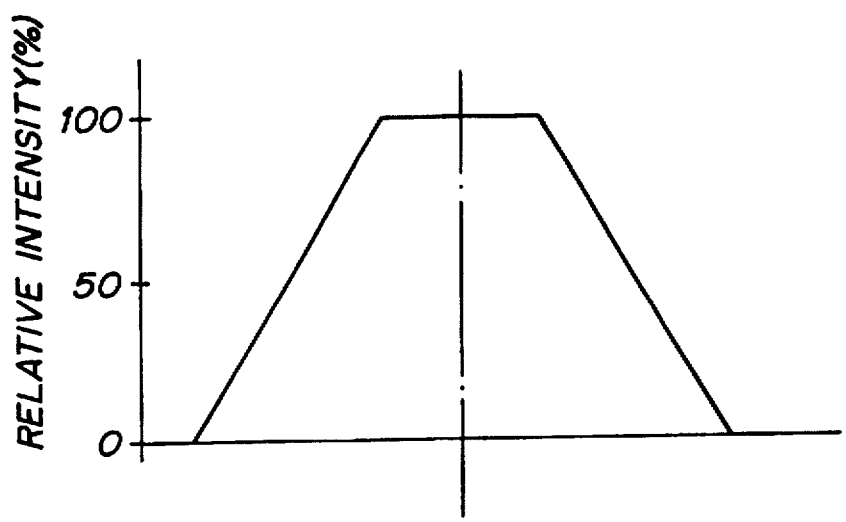
FIGS. 4(a) and 4(b) illustrate intensity profiles as a function of the diameter of the focused laser beam, measured at the cornea.
Figure 4B:
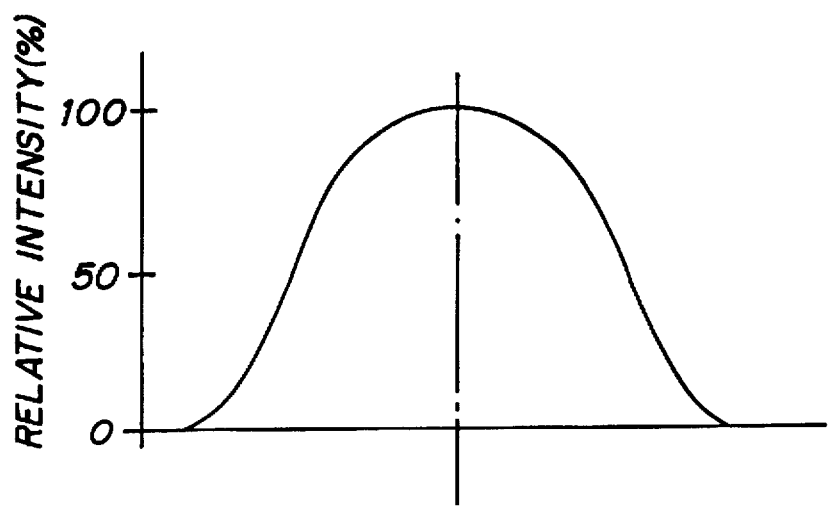

As shown in FIG. 4(a), the intensity profile of the focused laser beam 14 at the corneal surface ideally is contoured as a rotationally-symmetric trapezoid, in order to facilitate uniform irradiation of the treatment region 315, 325. The essentially gaussian profile shown in FIG. 4(b) approximates the idealized intensity profile illustrated in FIG. 4(a). It is noted that for smaller beam diameters, i.e., up to 2 mm, impinging on the corneal surface, the tissue removal profile for excimer ablation approximates a gaussian shape, independent from the beam intensity profile. For intermediate diameters, however, i.e., from 2 to 4 mm, the ablation profile approximates the beam intensity profile of the excimer laser beam. For larger diameters, i.e., from 4 to 7 mm or more, the ablation profile is deeper at the edge than the center compared to the beam intensity profile.

Photospallation is similar to the excimer ablation mechanism described above in that the beam intensity profile is generally not critical to the design or ablation pattern when using a spot size of 2 mm or smaller. Unlike photovaporization, where the tissue ablation mechanism is photothermal, the tissue ablation mechanism for photospallation is photomechanical. Therefore, the ablation pattern depends on the beam diameter, rather than a specific intensity profile. Thus, as a further advantage, since the present invention depends on pulse diameter and is not particularly sensitive to minor variations in the beam intensity profile, laser design issues may be relaxed.

BEAM TRANSFER OPTICS

As previously indicated, laser beam 10 is transferred to the main portion of the surgical apparatus 200 by means of beam transfer optics 30, shown in greater detail in FIGS. 5(a) and 5(b). It is noted that for the often crowded environment of an operating room, a flexible arrangement, whereby the beam delivery is effectively decoupled from the laser system, is preferred. As shown in FIG. 5(a), the beam transfer optics preferably includes a focusing lens 160 to condense the laser beam 10 into the entrance aperture of a decoupled guided means 162, such as a flexible fiber-optic cable. The fiber-optic cable 162 should preferably be capable of transmitting the intense infrared laser radiation over some distance, i.e., across an operating room, without damage to the fiber-optic cable itself, or significant loss of laser energy.

The fiber-optic cable 162 can be embodied as a single- or multiple-fiber bundle, and comprised of a material that safely transmits the specific wavelength of the laser 20, such as glass, sapphire, or another crystal. It is noted that in the infrared wavelength range, the additional losses associated with the added components required by the decoupled beam transfer optics 30 will generally be quite small. Alternatively, the laser beam can be coupled to the scanner system by means of a flexible hollow waveguide (not shown).

Preferably, the fiber-optic cable 162 connects the laser 20 to the main portion of the surgical apparatus 200 in a manner that permits convenient location of the laser 20 in the vicinity of the surgical apparatus 200, but not necessarily in a specific location. As shown in FIG. 5(a), the laser radiation exiting the output aperture 163 of the fiber cable 162 is captured by a relay lens 164 that forms an image of the output aperture 163. As shown in FIG. 1, this image is then propagated along paths 11, 12, 13 and 14 by means of partially-reflecting mirrors 50 and 60, to position the image at the anterior surface of the cornea of eye 70. The image plane of relay lens 164 is positioned during assembly of the apparatus so as to lie at the plane of best focus of microscope 80. The fiber-optic cable 162 may be embodied as the SapphIRe product, commercially available from Saphikon, Inc., or in accordance with the teachings of U.S. Pat. No. 5,349,590.

An alternate embodiment of the beam transfer optics 30 is shown in FIG. 5(b). The alternate arrangement of FIG. 5(b) replaces the fiber-optic cable 162 of FIG. 5(a) with a flexible articulated arm 166. The flexibility of the articulated arm 166, by rotation about axes B-C, C-D, D-E, E-F, and/or F-G, allows convenient location of the laser source 20 with respect to the main portion of the surgical apparatus 200, again without requiring the laser source 20 to occupy a specific location. Condensing and relaying of the laser radiation at input and output apertures of the articulated arm are accomplished by means of lenses 168 and 170 in a manner substantially as described for the corresponding optical components in FIG. 5(a). The articulated arm 166 may be embodied as the Light Guiding Arm, commercially available from Dantec measurements Technology, or in accordance with the teachings of U.S. Pat. No. 4,896,015.

Another alternate embodiment for the beam delivery system would place the laser on the arm of the surgical microscope in a fixed location with respect to the main portion of the surgical apparatus 200. Such an arrangement would require certain rigid relay means to transport the radiation, which may require greater care in optical alignment, while imposing additional packaging constraints. For these and other reasons, the decoupled means of FIG. 5(a) and FIG. 5(b) are preferred.

EYE TRACKER

The importance of proper centration of the treatment is generally recognized as an important factor for all PRK procedures. Misalignments of the eye 70 during the procedure are known to result in irregular astigmatism, glare phenomena, and decreased visual acuity and contrast sensitivity. Thus, as previously indicated, the surgical apparatus 200 preferably includes an eye tracker 100 which senses the motion of the eye 70 and provides signals that are proportional to the errors in lateral alignment of the eye 70 relative to the axis of the laser beam 14. An illustrative prior art eye tracking technique is disclosed in PCT Application No. WO 94/02007 to Knopp, et al, incorporated by reference herein.

The eye tracker 100 senses lateral movement of the patient's eye 70 by forming an optical image of a significant feature of the eye on an array 300 of detectors preferably arranged in the manner depicted in FIG. 6. The eye feature imaged by the eye tracker 100 is the approximately circular intersection 305 of the transparent cornea with the translucent and white-colored sclera constituting a structural member of the eyeball 70.

The intersection 305 is commonly known as the limbus of the eye 70. The limbus is approximately 12 mm in diameter in the human eye and is easily seen by virtue of its circular geometric contour and the inherent coloration of underlying ocular tissue seen through the transparent cornea as compared with the white sclera. In frontal view, transition at the limbus from the colored or tinted circular area and the white sclera offers photometric contrast in an axi-symmetric feature of the eye 70 that lends itself to tracking by the means described here. In a preferred embodiment, the contrast can be further enhanced by using red or near infrared filters in front of the detectors to make blue and green pupils appear as dark as brown pupils to the detector array 300.

When the limbus feature of the eye 70 is perfectly centered with respect to the axis of laser beam 14, the image of the limbus formed by lens 320 is centered on the detector array 300, as shown in FIG. 6(a). Under this centered condition, the four detectors comprising the array 300 each receive essentially equal amounts of energy from the image of the limbus 305 and, with the assistance of associated electronic means (not shown), create a null signal that is transmitted to tracking mirror 60 via connection 102 which serves to hold the mirror 60 stationary in its current position.

When the eye 70 is not perfectly centered with respect to the axis of the laser beam 14, however, the image of the limbus 305 formed at the detector array 300 is more or less decentered, as indicated schematically in FIG. 6(b). Under such a decentered condition, unequal amounts of light energy are deposited on the four detector elements comprising the array 300 and error signals proportional to the lateral displacement are created by the aforementioned associated electronics. These error signals are transmitted to the drive mechanism of mirror 60 causing the mirror 60 to deflect as required to return the image to its centered position.

Accordingly, the function of the eye tracker 100 is to maintain a centered condition between the axis of beam 14 and the cornea of eye 70. In this manner, the laser radiation delivered through beam 14 is applied to the cornea as if the eye had not moved from its nominal centered position. In addition, in order to allow for real-time tracking, the above-described tracking algorithm is preferably performed at least once for each interpulse duration. Thus, in the illustrative embodiment, where each pulse has a duration of less than 50 nanoseconds, at a repetition of 100 Hertz, there will be 10 milliseconds between pulses and the eye tracking response time is preferably less than 10 milliseconds.

It is understood that the scanning algorithm which is applied to mirror 50, in the manner described above, and the eye tracking function which is applied to mirror 60, could be combined and applied onto a single mirror, such as the mirror 60. In this embodiment, the mirror 50 would be a fixed mirror/beam splitter. This configuration could reduce hardware cost but would complicate the logical operation of the system and could increase the angular range requirements of the single mirror 60. Using two separate mirrors reduces the range requirements for each mirror and simplifies the design, manufacture, and testing of the separate scanning and eye tracking functions.

As previously indicated, frontal illumination of the eye 70, which is essential to proper functioning of the eye tracker 100, is provided by the coaxial illuminator 120 which may be integrated with the microscope 80. The illuminator 120 projects a tracking beam 17 onto the eye 70. Light reflected and scattered differentially by the cornea and underlying tissue and the adjacent sclera at the limbus 305 constitutes the object imaged by lens 320 at an appropriate magnification onto the detector array 300.

In a preferred embodiment of the invention, the wavelength of the illuminator beam 17 is chosen in the near infrared range of wavelength at approximately 0.8 to 1.0 microns. The sensitivity of the human eye is very low at those wavelengths so the portion of the beam 17 reflected by the cornea surface back into the microscope 80 will be so small as to not affect observation of the patient's eye by the surgeon 55 through the microscope 80. In addition, because of its low visibility to the eye 70, the near infrared frontal illumination also will not interfere with fixation of the eye by the patient upon the visible light sources, or targets, located within fixation target device 90.

Further, the intensity of the light source within illuminator 120 can be modulated at some convenient temporal frequency so as to further facilitate discrimination from unmodulated room ambient illumination or laser beam 14 by appropriate synchronous filtering within the electronics associated with the detectors of array 300. The detectors of the array 300 are not sensitive to the infrared radiation from laser source 20, so will not respond to laser beam 14 during operation of the eye tracker 100.

By virtue of the near angular coincidence of tracking beam 17 and laser beam 14, the specular reflection of tracking beam 17 from the cornea occurs near the center of the cornea and well inside the limbus 305. This reflection will therefore not interfere with the eye motion sensing function of the eye tracker system since it will not be imaged by lens 320 onto the detectors comprising array 300. It has been found that the use of a temporally modulated infrared light source, and the favorable choice of angular incidence of the beam 17 of illumination from said source onto the cornea of eye 70 constitute distinct improvements in the state of the art as represented by PCT Application No. WO 94/02007.

Figure 7:
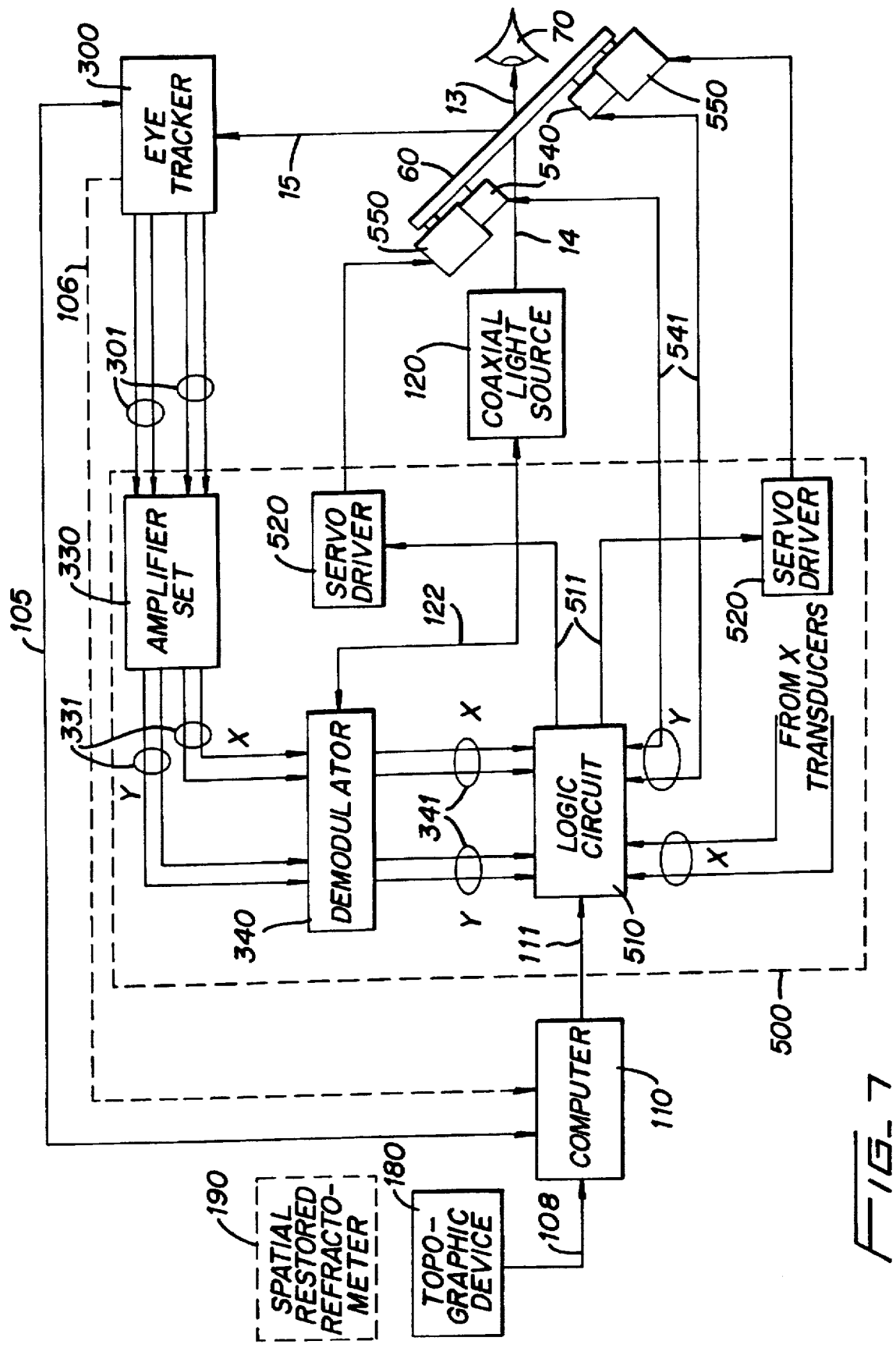
FIG. 7 is a schematic diagram of one embodiment of the electronic circuitry and servo control functions associated with the eye tracker indicated in FIGS. 1 and 2.

FIG. 7 shows, in schematic form, one embodiment of a servo system 500 used to drive the tracking mirror 60, along with the associated input signals from tracking detectors 300 contained within eye tracker 100 and related controls. In a preferred embodiment of the invention, the four detectors, collectively labeled 300 in FIG. 2, each comprise a single element PIN silicon photodetector, although dual-element detectors may alternately be selected, based upon specific functional requirements of the instrument.

Voltage signals 301 received from the detectors are subsequently fed into amplifier set 330, with the amplified signals 331 channeled directly into a demodulator 340. This demodulator is temporally synchronized, as indicated by control 122, with the tracking light source 120 used to illuminate the eye to ensure that only light of the appropriate frequency is selected for the tracking signals. As previously indicated, this synchronization constitutes a means for temporal differentiation of reflected light used for tracking, thus further enhancing signal levels over ambient light background. The gated signals 341 emerging from the demodulator are then fed into the logic circuit 510.

The logic circuit 510 comprises a key element of the servo subsystem, and serves as the central switchboard of the closed tracking feedback loop. The logic circuit converts the amplified and demodulated signals from the detectors of the array 300, corresponding to target position, into commands for controlling the tracking element, in this case, the tracking mirror 60. It is to be understood that diametrically opposing pairs of detectors produce varying electrical outputs as the image of the limbus 305 moves with respect to the X and Y axes, as indicated in FIG. 6.

The arithmetic difference between signals from each pair of opposing detectors is substantially proportional to the displacement of the image from the centered or null position in the corresponding axis. The signal differences produced within logic circuit 510 and further processed by the circuit 510 constitute mirror displacement commands indicated by controls 511. These displacement commands are relayed to the servo drivers 520 which, in turn, activate actuators 550 which are mechanically linked to mirror 60, thus causing the mirror 60 to pivot about its axes. In this manner, the angular orientation of the mirror 60 may be modified as required to pursue the target motion in two dimensions.

Transducers 540 are also mechanically connected to mirror 60 to provide feedback to logic circuit 510 via connections 541. The transducers 540 generally are comprised of position-sensing elements which, in a preferred embodiment, are simple, readily-available components. The transducers 540 allow stabilization of the motion of the tracking element, in this case mirror 60, referenced to a pre-selected default position. In addition, the transducers 540 sense when the tracking mirror 60 is at the end of its range and will no longer track the motion. This enables the computer 110 to stop the laser source 20, or to close shutter 40, when the tracker is no longer able to follow the eye motion.

In the preferred embodiment, the reference position of the mirror 60 corresponds to alignment of the patient's line-of-sight with the optical axis of the instrument, as previously discussed. This reference position can be selected by the computer 110, when the surgeon 55 indicates that the patient is aligned. Note that the collection of signals shown in FIG.

7, designated 301, 521, and 541 from the eye tracker 300 to the tracking mirror 60 were denoted collectively as connection 102 in FIG. 1. It is noted that for visual clarity, FIG. 7 illustrates only two of each of the four servo drivers 520, transducers 540 and actuators 550 that would be included in the illustrative servo system.

Like most servo systems, the system shown in FIG. 7 is an off-null measurement system based on returning the errors signals to zero. There may be alternative implementations of a servo control system other than the one depicted in FIG. 7 which would still allow the accurate measurement and/or control of eye displacements at sufficiently high rates. Such alternative servo systems are therefore included within the scope of the present invention.

TOPOGRAPHIC MEASUREMENTS

As previously indicated, a corneal topography device 180 may be used to assist in pre-op and post-op measurements of the eyes' shape or curvature. Any commercially available topographic instrument may be used for this purpose as long as it is modified to include reference targets for fixation as utilized by the present invention. An alternate embodiment would include in this location a Spatially Resolved Refractometer (SRR) 190 to measure true refraction across the cornea.

The ability to establish a common reference frame between different ophthalmic instruments is of further importance in consideration of the desirability of integrating the method of corneal surgery that is the subject of the invention with independent refractive and/or topographic measurements of the cornea. It is generally recognized that accurate measurement and determination of the refractive status of the eye is desirable for a successful outcome of any refractive surgical procedure.

Corneal topographic devices, such as those manufactured by EyeSys and Computed Anatomy, have had some utility in providing evaluation of pre- and post-operative shape of the cornea. Other instruments that have recently become available, such as the OrbScan product by Orbtek, Inc., may provide information about the local shape of the cornea which can be highly useful for optimizing the correction of certain types of refractive errors, such as astigmatism. For any of these instruments to be effective, however, it must be compatible with repeated measurements being referenced to the same location in the eye. This aspect can be provided by an eye tracking or fixation technique, in the manner described above, that is unique to a patient and not to an instrument. Inclusion of such an alignment feature may also allow intraoperative measurement of corneal topography which could be used as an active feedback during the procedure for the purpose of enhancing the precision of surgery and eliminating undesirable variables affecting predictability. Prior art as described by U.S. Pat. No. 5,350,374 to Smith shows the possibility of integrating an active feedback control loop based on a particular type of topographic instrument with a corneal surgery procedure.

In various embodiments, the present invention also seeks to include topographic feedback that is compatible with any number of available corneal measurement devices thus incorporating many of the advantageous features of the prior art devices, but enlarging their scope to include PRK surgery with a mid-infrared laser using a scanning beam delivery system.

An alternative to the shape mapping of these topography devices is the refraction mapping device and method called Spatially Resolved Refractometer (SRR). For a detailed discussion of SRR, see Webb, R. H., Murray Penny, C., Thompson, K. P., "Measurement of Ocular Local Wavefront Distortion with a Spatially Resolved Refractometer," *Applied Optics*, 31, 19, 3678–3686 (1992). The SRR device measures the refraction at each point on the cornea over the pupil by having a patient align two fixation sources through a small pinhole. This pinhole is translated across the cornea to map each point of the cornea with a separate refraction measurement. Since the purpose of PRK is to correct the refractive error of a patient, the SRR map is the ideal input for correction by the PRK system, providing an improvement over the refraction measured in a refracting lane, as well as the power map from a topography system. This preoperative input data may be used to help define the ablation profile and pattern. Alternatively, SRR may to used to map the eye during a procedure.

It is to be understood that the embodiments and variations shown and described herein are illustrative of the principles of this invention only and that various modifications may be implemented by those skilled in the art without departing from the scope and spirit of the invention.

We claim:

1. A medical apparatus for removing corneal tissue from an eye of a patient, said apparatus comprising:
   a laser source that produces pulses of mid-infrared radiation, wherein said infrared radiation has a wavelength approximately corresponding to a corneal absorption peak, and wherein said pulses have a duration of at least about 1 nanosecond; and
   a scanner-deflection means to direct the pulsed radiation across an area of said corneal tissue in a predefined pattern to remove portions of said corneal tissue primarily by photospallation.

2. The apparatus according to claim 1, wherein said corneal tissue is removed to correct the curvature of said cornea.

3. The apparatus according to claim 1, wherein said corneal tissue is removed to affect a therapeutic intervention.

4. The apparatus according to claim 1, wherein said beam has a pulse duration of less than about 50 nanoseconds.

5. The apparatus according to claim 1, further comprising an eye tracker means to sense and compensate for movements of the eye.

6. The apparatus according to claim 1, wherein said laser source is coupled to said scanner deflection means by a decoupled laser delivery system.

7. The apparatus according to claim 1, wherein said laser source is an erbium YAG laser producing infrared radiation at a wavelength of 2.94 microns.

8. The apparatus according to claim 1, wherein said pulsed beam is generated by a solid state laser emitting radiation in the range of approximately 1 to 2 microns and further comprising an optical parametric oscillator for frequency shifting said radiation to a wavelength of approximately 3 microns.

9. The apparatus according to claim 1, wherein said laser source is a solid state laser producing infrared radiation at a wavelength in the range 2.7 to 3.1 microns.

10. The apparatus according to claim 1, wherein the energy in each of said pulses is between about 5 mJ and about 30 mJ.

11. The apparatus according to claim 1, wherein said scanner deflection means produces a spot size in the range of about 0.3 mm to about 2 mm.

12. The apparatus according to claim 1, further comprising a corneal topography device for evaluating the shape of said corneal tissue.

13. The apparatus according to claim 1, wherein said corneal tissue is removed to alter the refractive properties of said eye and further comprising a spatially resolved refractometer for evaluating the refraction of said corneal tissue.

14. A method for removing corneal tissue from an eye of a patient, said method comprising the steps of:

generating a pulsed beam of laser radiation for ablating said corneal tissue, wherein said beam comprises mid-infrared radiation at a wavelength approximately corresponding to a corneal absorption peak, and wherein said beam has a pulse duration of at least about 1 nanosecond; and scanning said beam across an area of said corneal tissue in a predefined pattern to remove portions of said corneal tissue primarily by photospallation.

15. The method according to claim 14, wherein said corneal tissue is removed to correct the curvature of said cornea.

16. The method according to claim 14, wherein said corneal tissue is removed to affect a therapeutic intervention.

17. The method according to claim 14, wherein said beam has a pulse duration of less than about 50 nanoseconds.

18. The method according to claim 14, wherein said pulsed beam is generated by an erbium YAG laser producing infrared radiation at a wavelength of 2.94 microns.

19. The method according to claim 14, wherein said pulsed beam is generated by a solid state laser emitting radiation in the range of approximately 1 to 2 microns and further comprising the step of frequency shifting said radiation to a wavelength of approximately 3 microns utilizing an optical parametric oscillator.

20. The method according to claim 14, wherein said pulsed beam is generated by a solid state laser producing infrared radiation at a wavelength in the range 2.7 to 3.1 microns.

21. The method according to claim 14, further comprising the step of tracking the movement of said eye to ensure said beam is directed upon said corneal tissue.

22. The method according to claim 14, wherein said step of scanning said beam across said corneal tissue is performed in a discontinuous fashion to minimize collateral damage to said eye.

23. The method according to claim 14, wherein the energy in each of said pulses is between about 5 mJ and about 30 mJ.

24. The method according to claim 14, wherein said scanning step utilizes a spot size in the range of about 0.3 mm to about 2 mm.

25. The method according to claim 14, further comprising the step of evaluating the shape of said corneal tissue using an on-line corneal topography device.

26. The method according to claim 14, wherein said corneal tissue is removed to alter the refractive properties of said eye and further comprising the step of evaluating the refraction of said corneal tissue using a spatially resolved refractometer.

* * * * *

UNITED STATES PATENT AND TRADEMARK OFFICE
CERTIFICATE OF CORRECTION

PATENT NO.    : 5,782,822
DATED         : July 21, 1998
INVENTOR(S)   : Telfair et al.

It is certified that error appears in the above-identified patent and that said Letters Patent is hereby corrected as shown below:

Column 7,
Line 61, change "application No. WO 94/07908" to
-- application No. PCT/US94/07908 --

Column 12,
Lines 26 and 27, change "PCT application No. WO 94/02007 to Knopp et al." to
-- PCT application No. PCT/US94/02007 to Knopp et al. --.

Signed and Sealed this

Second Day of September, 2003

JAMES E. ROGAN
*Director of the United States Patent and Trademark Office*